(12) United States Patent
Hojsgaard et al.

(10) Patent No.: US 9,133,430 B2
(45) Date of Patent: Sep. 15, 2015

(54) APPARATUS FOR PRODUCTION OF BIOGAS BY DIGESTION OF ORGANIC MATERIAL

(75) Inventors: Soren J. Hojsgaard, Hillerod (DK); Bente E. Nielsen, Charlottelund (DK); Per Koefoed-Hansen, Frederikssund (DK)

(73) Assignee: Veolia Water Solutions and Technologies Support, Saint Maurice (FR)

( * ) Notice: Subject to any disclaimer, the term of this patent is extended or adjusted under 35 U.S.C. 154(b) by 214 days.

(21) Appl. No.: 13/984,686

(22) PCT Filed: Feb. 8, 2012

(86) PCT No.: PCT/EP2012/052128
§ 371 (c)(1),
(2), (4) Date: Sep. 13, 2013

(87) PCT Pub. No.: WO2012/107489
PCT Pub. Date: Aug. 16, 2012

(65) Prior Publication Data
US 2014/0024108 A1    Jan. 23, 2014

(30) Foreign Application Priority Data
Feb. 11, 2011  (EP) ...................................... 11154168

(51) Int. Cl.
*C12M 1/107*   (2006.01)
*C12M 1/00*    (2006.01)

(52) U.S. Cl.
CPC ............... *C12M 21/04* (2013.01); *C12M 23/34* (2013.01); *C12M 23/36* (2013.01); *C12M 47/20* (2013.01); *Y02E 50/343* (2013.01)

(58) Field of Classification Search
CPC ...... C12M 21/04; C12M 23/34; C12M 23/36; C12M 47/20; Y02E 50/343
See application file for complete search history.

(56) References Cited

U.S. PATENT DOCUMENTS 3,869,087 A    3/1975   Erickson
4,429,643 A *  2/1984   Mulholland ................... 110/238

FOREIGN PATENT DOCUMENTS

CN    101812401 A    8/2010
WO    2008/093044 A1  8/2008

* cited by examiner

*Primary Examiner* — Nathan Bowers
*Assistant Examiner* — Gautam Prakash
(74) *Attorney, Agent, or Firm* — Coats & Bennett PLLC

(57) ABSTRACT

An apparatus for production of a biogas by anaerobic digestion of organic material, the apparatus comprising: a digester chamber defining: a gas generating zone and a gas collecting zone. A biogas outlet is defined in the gas collecting zone, and one or more nozzles is/are arranged to spray a gas cooling liquid into the gas accommodated in the gas collecting zone so as to cool the gas. A collecting member is arranged in the gas collecting zone to collect the gas cooling liquid when sprayed from the one or more nozzles towards the collecting member so as to prevent the gas cooling liquid from entering the organic material. The collecting member is arranged to cause the collected gas cooling liquid to flow into a liquid based safety valve.

16 Claims, 6 Drawing Sheets

APPARATUS FOR PRODUCTION OF BIOGAS BY DIGESTION OF ORGANIC MATERIAL

This application is a U.S. National Stage Application of PCT Application No. PCT/EP2012/052128, with an international filing date of 8 Feb. 2012. Applicant claims priority based on European Application No. 11154168.1 filed 11 Feb. 2011. These applications are incorporated herein by reference in their entirety.

FIELD OF THE INVENTION

The present invention relates to an apparatus for production of biogas. In particular the present invention relates to an apparatus comprising a gas collector, a safety valve, a gas cooling means, and a gas outlet.

BACKGROUND OF THE INVENTION

Digestion in anaerobic digesters is part of the treatment process in many municipal and industrial plants. The purpose of the digestion which can be either cryophilic, mesophilic or thermophilic is to convert part of the organic material to biogas utilised for production of electricity and/or heat. At the same time the digester reduces the amount of solids, whereby the quantity of material to be disposed subsequently from the treatment plant is reduced.

It is an object of one or more embodiments of the present invention to simplify current anaerobic digesters.

DESCRIPTION OF THE INVENTION

In a first aspect the present invention relates to an apparatus for production of a biogas by anaerobic digestion of organic material, the apparatus comprising:
  a digester chamber defining:
    a gas generating zone for accommodation of the organic material which when accommodated in the gas generating zone generates the biogas by digestion of the organic material; and
    a gas collecting zone at least a part of which is located above the gas generating zone in the digester chamber to collect the biogas generated in the gas generating zone;
wherein a biogas outlet is defined in the gas collecting zone, the biogas outlet being arranged such that biogas exits the gas collecting zone through the biogas outlet;
wherein one or more nozzles is/are arranged in the gas collecting zone, the nozzles being adapted to spray a gas cooling liquid into the gas accommodated in the gas collecting zone so as to cool the gas;
wherein a collecting member is arranged in the gas collecting zone to collect the gas cooling liquid when sprayed from the one or more nozzles towards the collecting member so as to prevent the gas cooling liquid from entering the organic material;
wherein one or more safety valves are arranged in the gas collecting zone, each safety valve defining an inlet which is fluidly connected to the interior of the gas collecting zone and an outlet which is fluidly connected to the air outside the apparatus; and
wherein at least one of the one or more safety valves is a liquid based safety valve and wherein the collecting member is arranged to cause the collected gas cooling liquid to flow into the liquid based safety valve.

One advantage of arranging the collecting member such that the collected gas cooling liquid flows into the liquid based safety valve is, that the collected gas cooling liquid is prevented from flowing into the organic material. This is desirable as such entry of the collected gas cooling liquid would cause the organic material to be diluted with the result that the organic material would reside in the gas generating zone for a shorter period of time. The result of the latter would be that a lower percentage of the organic material would be digested and whereby the gas production would decrease.

One other advantage of the present invention is that by guiding the collected gas cooling liquid into the liquid based safety valve, it is ensured that the liquid based safety valve does not run dry by evaporation. If the latter happened, the liquid based safety valve would cease to function. Depending on the design of the system this could cause the biogas to escape the apparatus in an uncontrolled manner and thus increase the risk of explosions.

Another advantage of the present invention is that the liquid sprayed into the gas collection chamber by means of the nozzles may be used to prevent fire and/or explosions whereby the nozzles functions as flame/explosion arrestors.

The apparatus is adapted to produce biogases e.g. containing methane and carbon dioxide as main components.

Examples of the organic material are sludge from treatment of industrial or municipal wastewater, waste from farms and agriculture, energy crops, household waste, waste from industrial productions.

The digester chamber may be symmetric about a vertical line such as rotationally symmetric about a vertical line. Alternatively, the digester chamber may be asymmetric e.g. such that the gas collecting zone is defined in one side of the chamber.

The digester may be defined by a concrete material or a metal material. The height of the digester may be in the range 1 to 100 meters, such as 10 to 50 meters.

The width of the digester may be in the range 1 to 100 meters such as 10 to 50 meters.

The volume of the digester may be in the range 1 to $10^6$ m$^3$, such as $10^3$ to $10^4$ m$^3$.

The digester may define a waste inlet for flow of organic material into the digester. Moreover, the digester may comprise a waste outlet for flow of organic material out of the digester. In one embodiment, waste inlet is used to allow untreated and/or partially treated organic material to enter the digester. The waste outlet may in one embodiment, be used to allow treated and/or partially treated waste to exit the digester. The partially treated organic material may be organic material which have already been subjected to biogas production but which still contains biological material which can produce biogas.

In one embodiment, the waste inlet is positioned in the lower part of the gas generating zone while the waste outlet is positioned in the upper part of the gas generating zone.

In an alternative embodiment, the waste inlet is positioned in the upper part of the gas generating zone while the waste outlet is positioned in the lower part of the gas generating zone.

A pump may be arranged to pump the organic material into the digester. Alternatively, or as a supplement, a pump may be arranged to pump treated organic material out of the digester.

In one embodiment, at least a part of the gas generating zone is positioned below any part of the gas collecting zone. Moreover, at least a part of the gas collecting zone may be positioned above any part of the gas generating zone. In one embodiment, any part of the gas collecting zone is positioned above any part of the gas generating zone.

The upper part of the gas generating zone may be shaped so as to guide the gas generated into the gas connecting zone. In one embodiment, the upper parts of sidewalls and/or a ceiling of gas generating zone defines inclined surfaces which are adapted to guide the generated gas into the gas collecting zone.

In one embodiment, the width of the gas collecting zone is in the range 0.2 to 20 meters, such as 1 to 15 meters, such as 5-10 meters. In one embodiment, the height of the gas collecting zone is in the range 0.2 to 20 meters, such as 1 to 15 meters, such as 5-10 meters. In one embodiment, the volume of the gas collecting zone is in the range of 0.0008 to 8000 m$^3$, such as in the range 1 to 5000 m$^3$, such as in the range 1000 to 2500 m$^3$.

In one embodiment, the gas collecting zone comprises no bottom floor. In another embodiment, one or more—such as all—sidewalls of the gas collecting zone forms an elongation of one or more—such as all the sidewalls of the gas generating zone. In one embodiment, the transition between en upper ceiling of the gas generating zone and one or more sidewalls of the gas collecting zone defines no flow restricting means.

In one embodiment, the gas generating zone and the gas collecting zone are defined by the same chamber, i.e. such that no pipes or tubes interconnect the two zones. In one embodiment, the lower part of the gas collecting zone is as wide as that part of the gas generating zone which lead into the gas collecting zone. In one embodiment, the lower half of the gas collecting zone is as wide as that part of the gas generating zone which leads into the gas collecting zone. The latter part may be the highest possible part of the gas collecting zone.

In one embodiment, width of the gas generating zone and the gas collecting zone does not increase in the direction from the gas generating zone towards the biogas outlet of the gas collecting zone.

The digester may be gas tight relative to its surroundings such that gas can only escape through the biogas outlet of the gas collecting zone.

The biogas outlet is defined in the gas collecting zone and is arranged such that biogas exits the gas collecting zone through the biogas outlet. In one embodiment, more than one bio gas outlet is provided such as one, two, three, four, five etc. The biogas outlet(s) may be arranged in the upper half of the gas collecting zone, such as in the upper third, such as in the upper fourth, such as in the upper fifth. In one embodiment, one or more of the biogas outlets is/are defined in the uppermost part of the gas collecting zone.

One or more nozzle(s) is/are arranged in the gas collecting zone. The nozzles are adapted to spray a gas cooling liquid into the gas accommodated in the gas collecting zone so as to cool the gas. It will be appreciated that in order to cool the gas, the temperature of the gas cooling liquid must be lower than the temperature of the gas. In one embodiment, the temperature of the gas cooling liquid is below 50 degrees Celsius, such as below 40 degrees Celsius, such as below 30 degrees Celsius, such as below 20 degrees Celsius, such as below 10 degrees Celsius. The nozzles may be distributed over an area of a ceiling of the gas collecting zone.

The apparatus may be connected to a supply of cleaned waste water which is sprayed into the gas collection chamber by means of the nozzles.

The collecting member is arranged in the gas collecting zone to collect the gas cooling liquid when sprayed from the one or more nozzles towards the collecting member. Thereby the gas cooling liquid is prevented from entering gas generation zone and thus from being mixed with the organic material. The nozzles may be arranged such that the liquid sprayed therethrough can only hit the collecting member. In some embodiments, the nozzles may also be arranged such that the liquid when sprayed out through the nozzles may also hit any surface above the collecting member which guides the liquid onto the collecting member.

As gas is generated in the digester, the digester comprises safety valves which are adapted to allow passage of gas when the pressure inside the digester is above a predetermined threshold. This threshold may be above 2000 Pa, such as above 5000 Pa.

At least one of the one or more safety valves is a liquid based safety valve which is arranged such with respect to the collecting member, that any gas cooling liquid collected by the collecting member is guided into the liquid based safety valve whereby a predetermined water level in the water based safety valve is maintained. The liquid based safety valve may be a water trap.

In one embodiment, the collecting member defines an upper and a lower surface. In order to collect the gas cooling liquid, the upper surface may face the nozzles which are arranged above the collecting member. Moreover, the lower surface may be arranged such that it faces the gas generating zone in which the organic material is accommodated. Thus when the gas ascends from the organic material and into the gas collecting zone of the digester, it may flow towards or into contact with the lower surface of the collecting member. Depending on the temperature of the lower surface the gas may be cooled to some extend. It will be appreciated that when a cold gas cooling liquid is sprayed onto the upper surface of the collecting member, the upper surface of collecting member is cooled. Thus in embodiments where no thermal insulator is provided between the upper and the lower surface, the lower surface will also be cooled. In order to avoid this, a thermal insulator may be provided between the upper and the lower surface. Thus, the collecting member may be provided in the form of a sandwich construction in which a thermally insulating member defines a core of the sandwich construction. In another embodiment, the thermal insulator is secured to the lower surface of a plate e.g. a metal plate, whereby the surface which faces the organic material is insulated relative to the upper surface of the plate.

In one embodiment, the collecting member is inclined relative to a horizontal direction so as to guide the collected gas cooling liquid towards the at least one liquid based safety valve. The inclination of the collecting member relative to the horizontal direction may be between 5 and 45 degrees, such as between 20 and 30 degrees. The upper surface of the collecting member may be plane. Alternatively, the upper surface of the collecting member may be concave or convex.

The collecting member may be arranged such that the gas cooling liquid which is collected during use drips into the liquid based safety valve. The dripping gas cooling liquid may fall from the collecting member and directly into a surface of the liquid contained in the liquid based safety valve. Alternatively, or as a supplement, the dripping gas cooling liquid may fall from the collecting member and directly onto a surface of the liquid based safety valve which is not an upper surface of the liquid contained therein. After having hit this non-liquid surface the liquid may flow into the liquid contained in the liquid based safety valve.

Furthermore, the lowest point of the collecting member may be positioned directly above the inlet of the liquid based safety valve(s). In one embodiment this means that during operation of the apparatus, a vertical line extends through the lowest point of the collecting member and a liquid surface of the liquid based safety valve.

The liquid based safety valve may define a liquid outlet which is arranged to allow excess liquid from the liquid based safety valve to exit the liquid based safety valve therethrough.

Moreover, the liquid based safety valve may define a first and a second liquid trap which are arranged in series or in parallel. When the first and the second liquid traps are arranged in series any liquid flowing out of the first liquid trap may subsequently flow into the second liquid trap.

In one embodiment, the liquid based safety valve defines a gas outlet which is arranged such that gas will escape the liquid based safety valve therethrough when the first liquid trap does not contain a predetermined amount of liquid. This may be the case when the pressure inside the digester exceeds a predetermined threshold, whereby the liquid contained in the first liquid trap flows into the second liquid trap and/or is blown out of the gas outlet of the liquid based safety valve. As a consequence, the gas is prevented from entering the liquid exit. As the liquid exit often will be connected to pipes and tubes e.g. sewers it is undesirable that the gas is guided into such pipes and tubes. Thus by providing the gas outlet, the gas may be directed into the surrounding air. It will be appreciated that the gas outlet may be arranged at an elevated position such that the gas is not emitted near the ground.

In order to be able to maintain the liquid based safety valve, the liquid based safety valve may be accessible from an outer surface of the apparatus. In one embodiment, the liquid based safety valve is slidably arranged in the apparatus such that that it is slidable between an inserted position in which it is positioned inside the apparatus in the gas collecting zone thereof, and a removed position in which it is accessible outside the apparatus. Alternatively, or as a supplement, the liquid based safety valve may be pivotally connected to the structure defining the gas collecting zone.

In some situations, it may be desirable to open the first liquid trap such that the generated gas is guided out through the gas outlet. Thus in one embodiment, the first and the second liquid traps defines a first and a second liquid zone, respectively, in which liquid is provided during operation. The first and the second liquid zones may be fluidly connected such that when a by-pass valve is in an open state liquid may flow from the first liquid zone to the second liquid zone, while liquid is prevented from flowing from the first to the second liquid zone thought the by-pass valve, when the by-pass valve is in a closed state.

During use of the digester, the organic material may generate foam which gradually will ascend from the organic material and up towards collecting member and further up towards the gas outlet. This foam is undesired as it may deposit on the inner surfaces of the gas outlet and the tubes/pipes connected thereto. Thus in one embodiment, the nozzles are arranged such that when the gas cooling liquid is sprayed out through the nozzles, the gas cooling liquid is sprayed into the a foam which during use of the apparatus is generated by the organic material whereby it ascends from the gas generating zone into the gas collecting zone in which it continues towards the one or more biogas outlets. The one or more nozzles may be adapted to spray an amount of the gas cooling liquid sufficient to prevent the foam from entering the biogas outlet. Moreover, the nozzles may be adapted to function as fire and/or explosion preventing means.

In one embodiment, the collecting member is arranged relative to the water based safety valve such that gas and/or foam is prevented from passing between the collecting member and the liquid based safety valve. This may e.g. be achieved omitting the provision of a passage between the collecting member and the liquid based safety valve. In order to allow the gas to enter the biogas outlet, the collecting member may be arranged such with respect to an inner wall of the gas collecting zone that gas and/or foam may be pass between the inner wall and the highest point of the collecting member.

BRIEF DESCRIPTION OF THE FIGURES

The invention will now be described with reference to the figures in which.

DETAILED DESCRIPTION OF THE FIGURES

Figure 1:
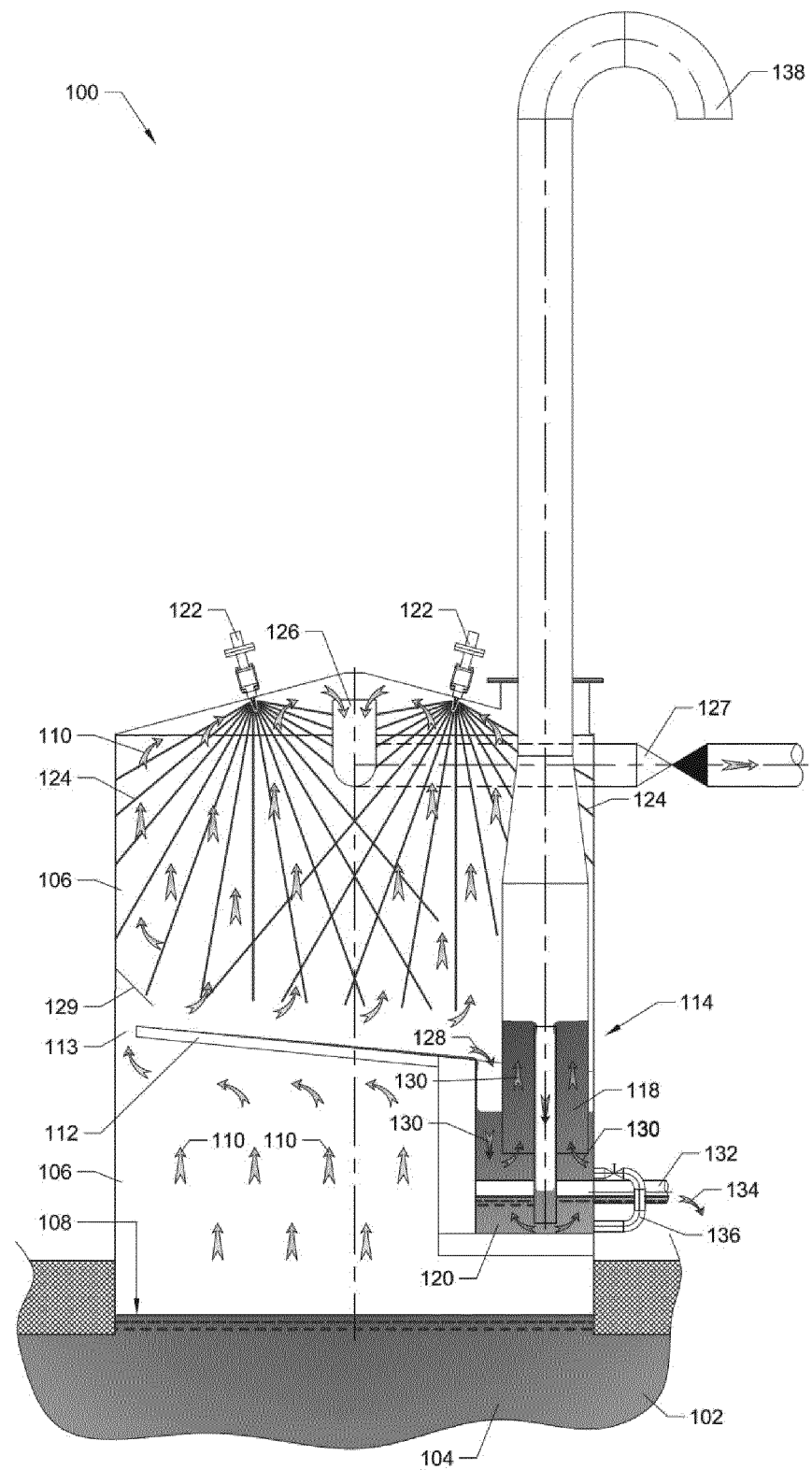
FIG. 1 discloses a first embodiment of the apparatus for production of biogas wherein the first liquid trap is closed, FIG. 2 discloses the second embodiment of the apparatus for production of biogas wherein the first liquid trap is open, FIG. 3 discloses a second embodiment of the apparatus for production of biogas wherein the first liquid trap is closed, FIG. 4 discloses the second embodiment of the apparatus for production of biogas wherein the first liquid trap is open, FIG. 5 discloses an isometric view of the apparatus for production of biogas, and FIG. 6 discloses a cross-sectional view of the entire apparatus for production of biogas.
Figure 2:
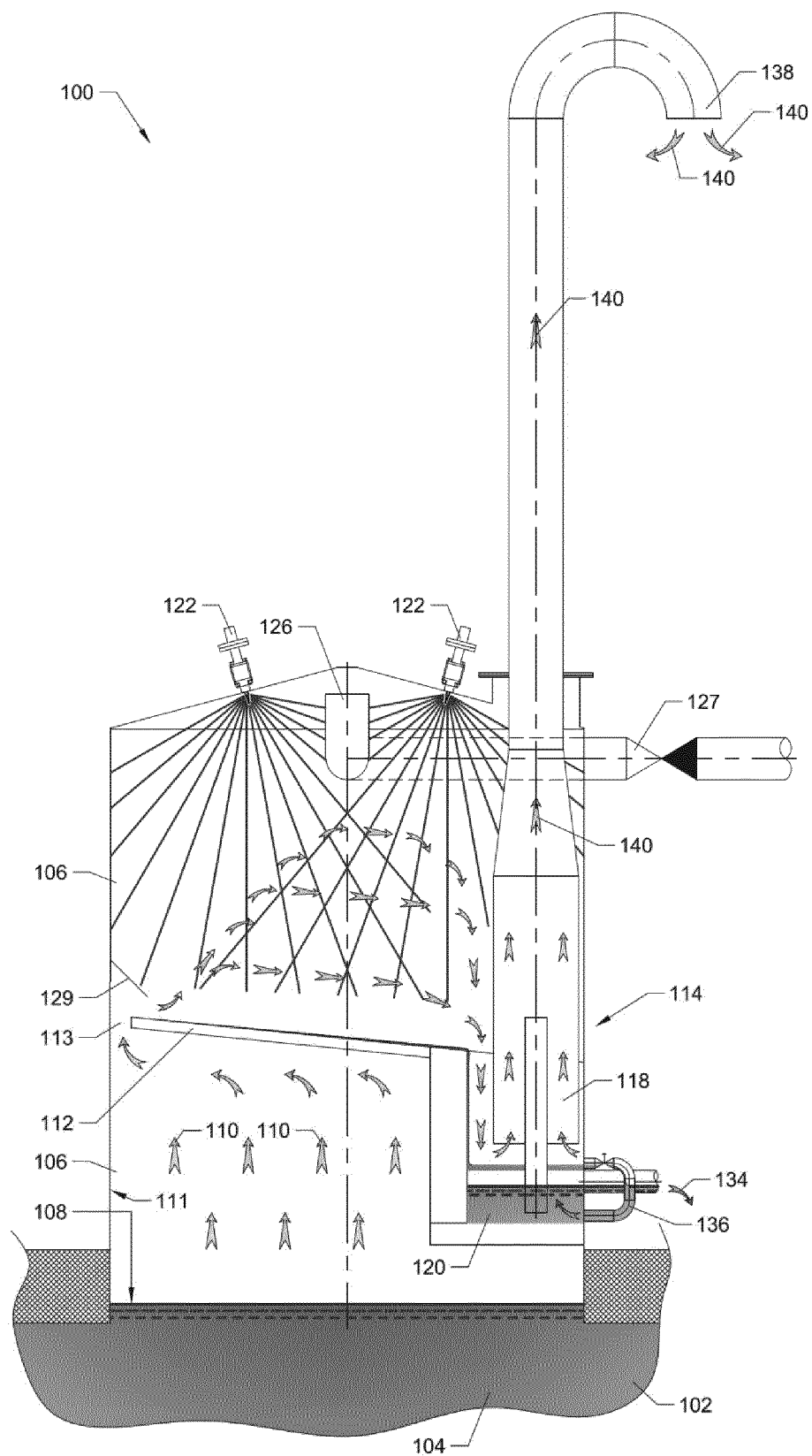

FIG. 1 discloses an apparatus for production of biogas 100 by digestion of organic material 102. The apparatus for production of biogas 100 defines a gas generating zone 104 and a gas collecting zone 106 which is arranged above the gas generating zone 104. In the embodiment of FIGS. 1 and 2, the upper surface 108 of organic material 102 is defined in the upper part of the gas generating zone 104. Any biogas generated by the organic material 102 will ascend from the gas generating zone 104 and into the gas collecting zone 106 as is indicated by arrows 110. Due to the provision of the collecting member 112, the gas is guided between the collecting member 112 and an inner surface 111 of the gas collecting zone 106 through a passage 113 defined therebetween. The liquid based safety valve 114 defines a first water trap 118 and a second water trap 120. The liquid traps 118, 120 are arranged in series such that the first water trap 118 is provided upstream relative to the second water trap 120. In the embodiment of FIG. 1, both the liquid traps 118, 120 are filled with water and thus closed, whereas only the second water trap 120 is filled with water and thus closed in the case of FIG. 2.

Accordingly in the embodiment of FIG. 1, the gas will be prevented from entering the first water trap 118 as long at the gas pressure is below a predetermined threshold which is determined by the design of the first water trap 118. The result is that the biogas continues upwards in the gas collecting zone 106. In the upper part of the gas collecting zone 106 a plurality of nozzles 122 are provided. In use a gas cooling liquid 124 is sprayed into the biogas whereby it is cooled prior to exiting the gas collecting zone 106 through the biogas outlet 126. A uni-directional valve 127 may be provided in the outlet 126 or downstream relative thereto (as is the case in FIGS. 1 and 2) such that a pressure drop in the gas collecting zone 106 does not cause a flow of the collected gas back into the gas collecting zone 106.

The collecting member 112 is adapted to prevent the gas cooling liquid 124 from entering the organic material 102, as it is arranged to collect the gas cooling liquid 124. As the collecting member 112 is inclined relative to the horizontal direction, the collecting member 112 guides the collected gas cooling liquid into the first water trap 118 by means of gravity. This is indicated by arrow 128. Moreover a passage shield 129 is arranged to prevent the gas cooling liquid from entering the passage 113 and thus from entering the organic material. In the embodiment of FIGS. 1 and 2 the collecting member 112 and the liquid based safety valve are integrated such that no passage is defined therebetween.

In the first water trap 118, the collected gas cooling liquid 124 flows into the second water trap 120. This is indicated by arrow 130. In the second water trap 120, the gas cooling liquid 124 flows out through the liquid outlet 132 as is indicated by arrow 134.

In the embodiment of FIG. 2, the first water trap 118 is open as the liquid is no longer present therein. This may be due to the by-pass valve 136 being open or due to a blow out of the liquid in the first water trap 118 as a result of the pressure in the gas collecting zone 106 being above the predetermined threshold. The result is that the gas may escape the outlet 138 as is indicated by arrow 140. It will be appreciated that the provision of the second liquid trap 120 ensures that the gasses will not enter the liquid outlet 132. Instead the biogas exits the gas outlet 138.

Figure 3:
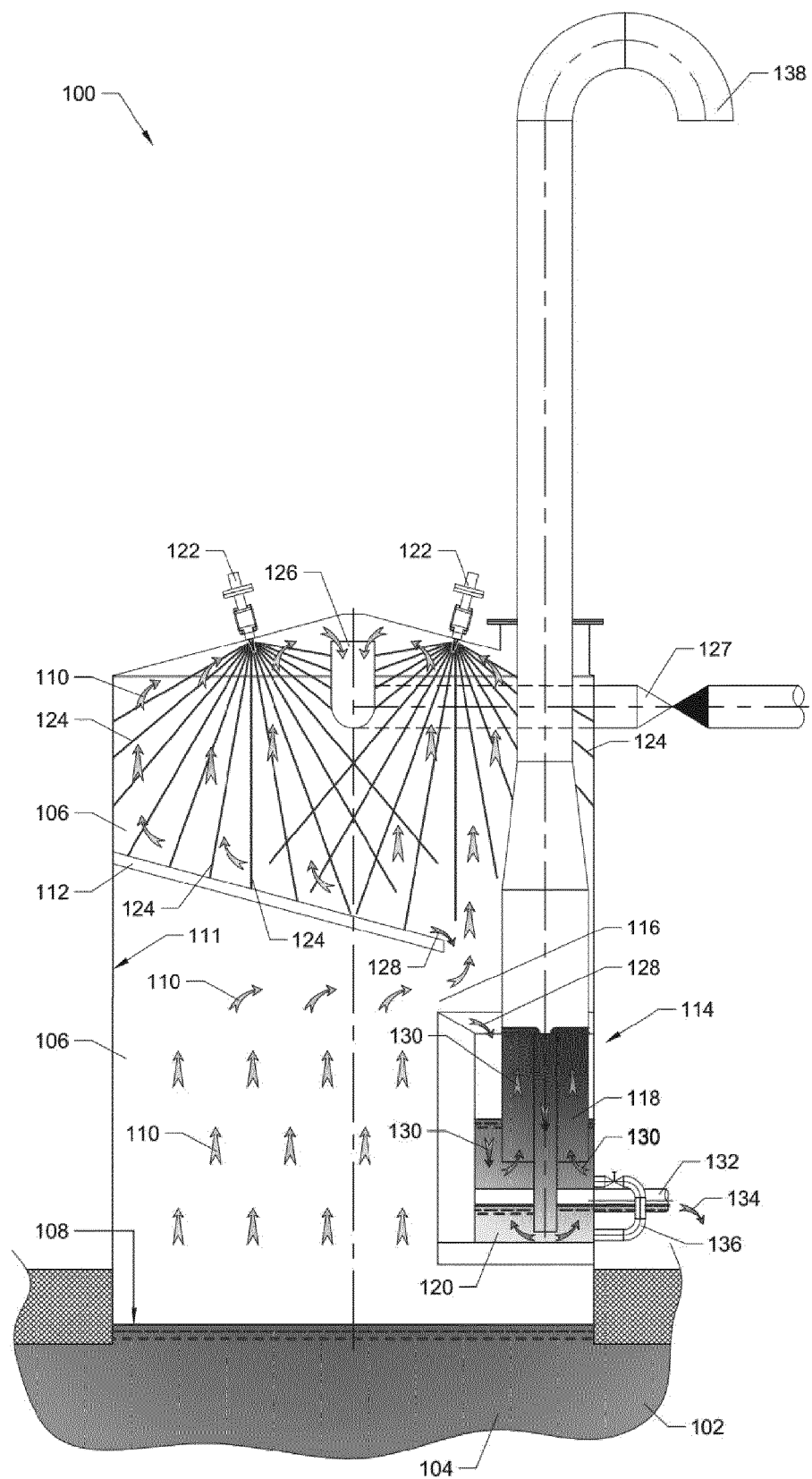
Figure 4:
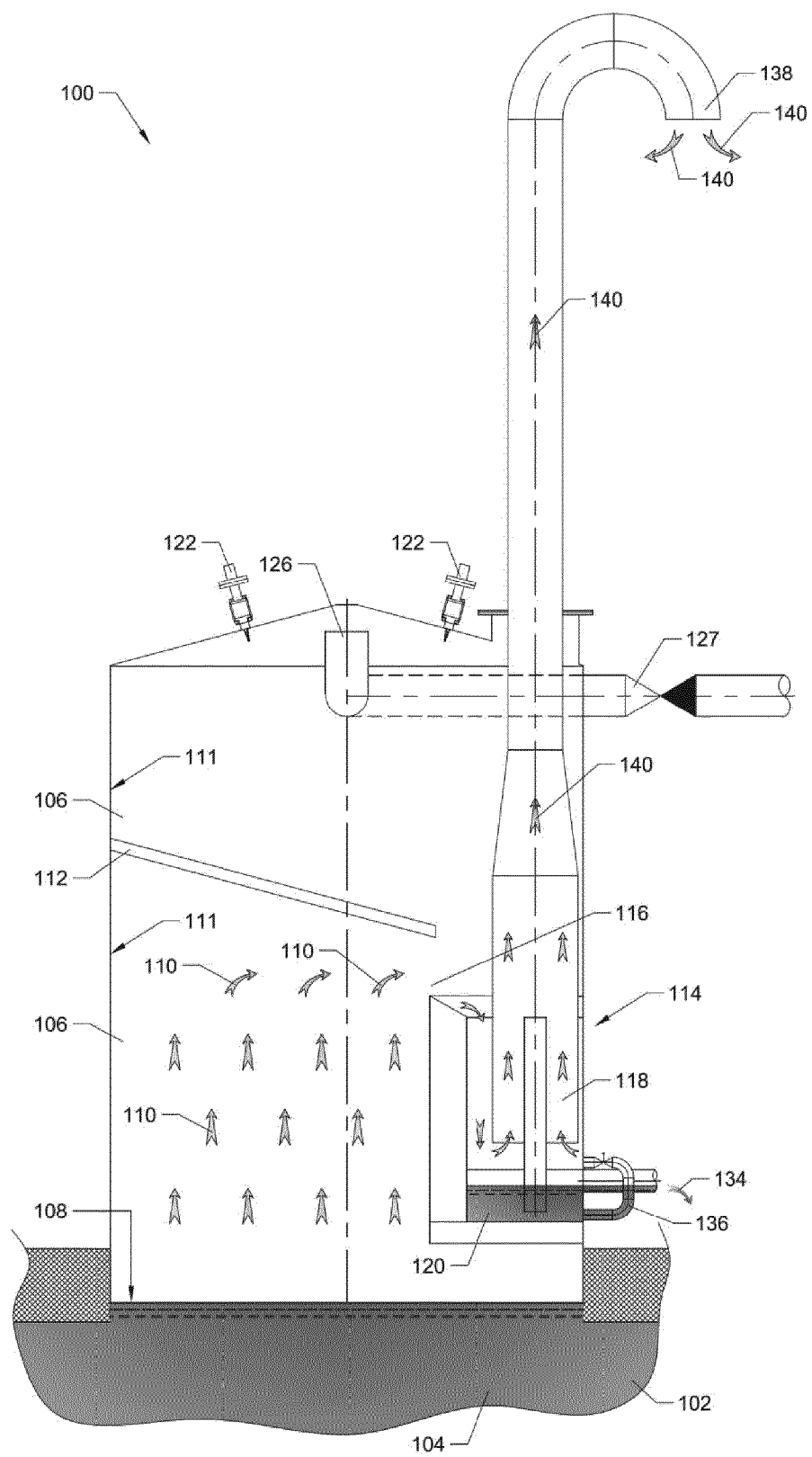

In FIGS. 3 and 4 disclose second embodiment of the present invention. Many of the elements of these two figures are identical to the elements of FIGS. 1 and 2. Thus, identical reference numbers refer to identical elements. The difference between the two figures is the arrangement and the position of the collecting member 112. In FIGS. 1 and 2 the collecting member 112 is arranged such that the passage 113 is defined between the collecting member 112 and the inner surface 111 of the gas collecting zone 106. In FIGS. 3 and 4, the passage 113 is not defined. Instead the upper part of the collecting member 112 is in direct contact with the inner surface 111 of the gas collecting member 106. In order to allow the biogas to flow towards the biogas outlet 126, a passage 116 is defined between the lower part of the collecting member 112 and the liquid based safety valve 114. In order to ensure that the gas cooling liquid collected by means of the collecting member does not enter into the organic material, the lowest part of the collecting member 112 is arranged directly above the liquid based safety valve 114. Thus, the collected liquid flows/drips into the liquid base safety valve 114 with the effect that it is constantly supplied with liquid and thereby prevented from running dry due to evaporation of liquid contained therein.

Figure 5:
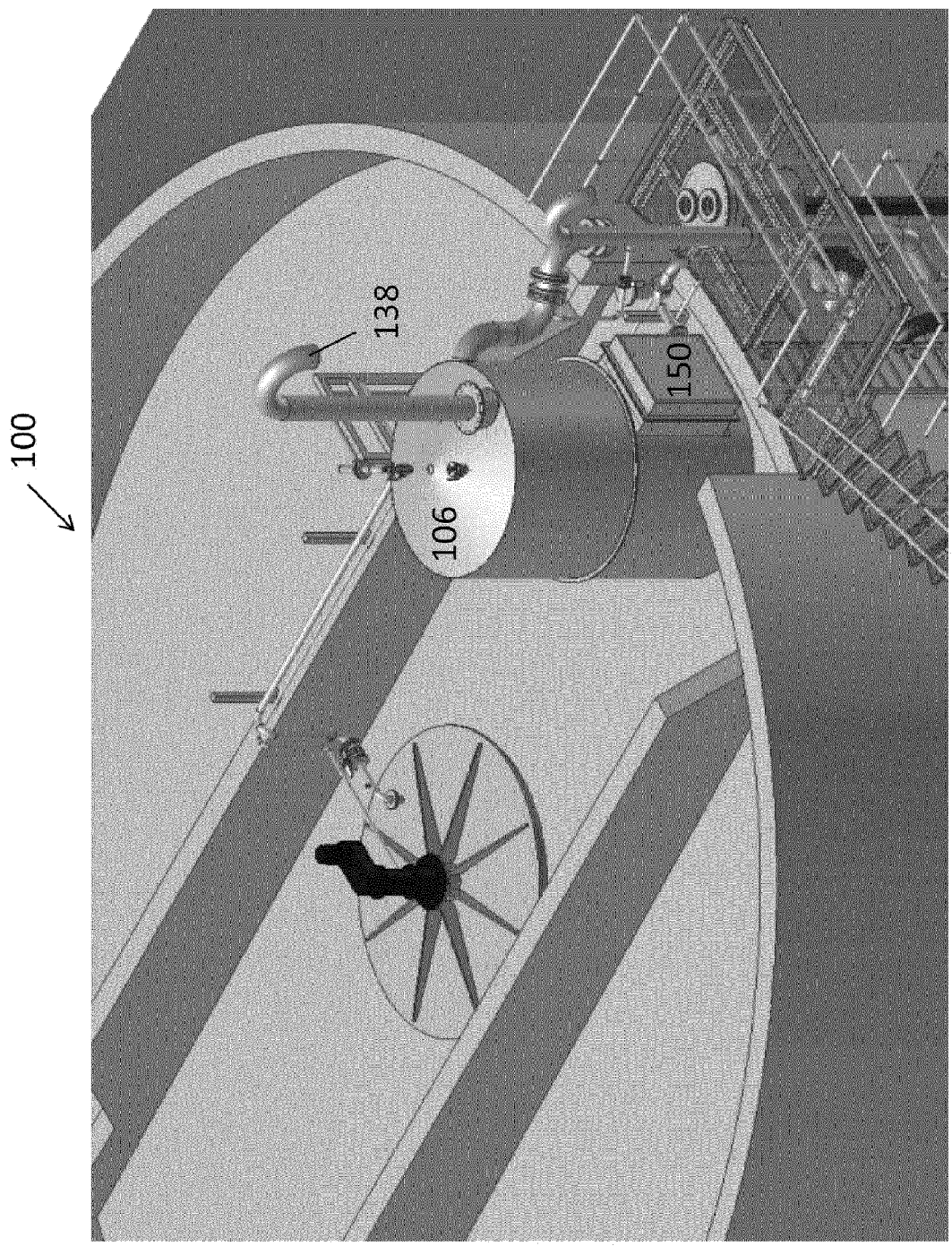
Figure 6:
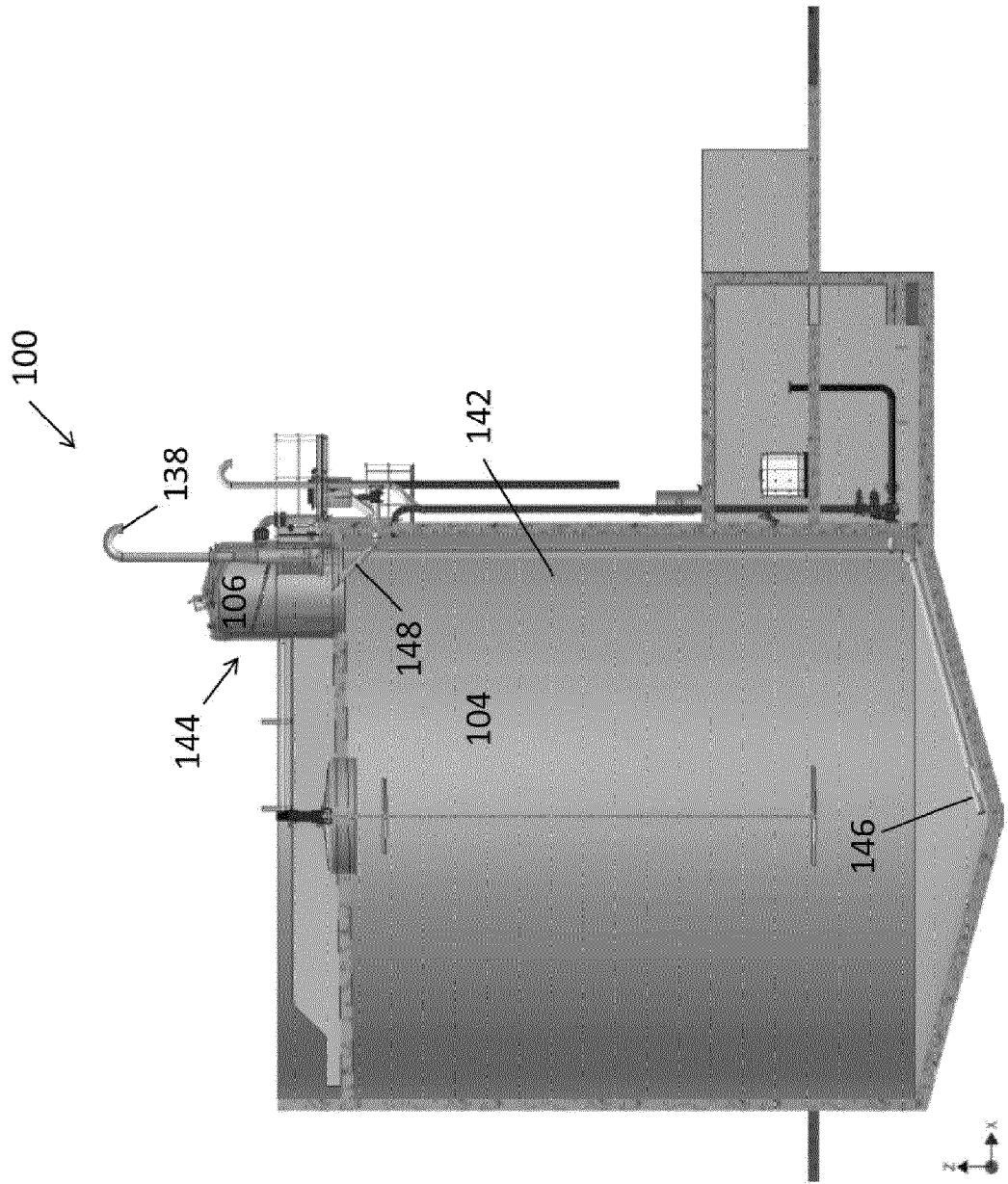

FIGS. 5 and 6 disclose an isometric view and a cross-sectional view respectively of the apparatus for production of biogas 100. In FIG. 4 the apparatus for production of biogas 100 is seen from above. In both drawings it may be seen that the digester is defined by a large structure 142 which defines the gas generating zone 104 and by a smaller structure 144 on top of the larger structure 142. This smaller structure 144 defines the gas collecting zone 106. In gas generating zone 104 a waste inlet 146 is provided for feeding the waste material into the gas generating zone 104 and a waste outlet 148 is provided through which the organic material exits the gas generating zone 104. A latch 150 is defined in the smaller structure 144. When the latch 150 is opened the liquid traps 118, 120 may be accessed and thus serviced.

The invention claimed is:

1. An apparatus for production of a biogas by anaerobic digestion of organic material, the apparatus comprising:
   a digester chamber defining:
   a gas generating zone for accommodation of the organic material which when accommodated in the gas generating zone generates the biogas by digestion of the organic material; and
   a gas collecting zone which is located above the gas generating zone in the digester chamber to collect the biogas generated in the gas generating zone;
   wherein a biogas outlet is defined in the gas collecting zone, the biogas outlet being arranged such that biogas exits the gas collecting zone through the biogas outlet;
   wherein one or more nozzles is/are arranged in the gas collecting zone, the nozzles being adapted to spray a gas cooling liquid into the gas accommodated in the gas collecting zone so as to cool the gas;
   wherein a collecting member is arranged in the gas collecting zone to collect the gas cooling liquid when sprayed from the one or more nozzles towards the collecting member so as to prevent the gas cooling liquid from entering the organic material;
   wherein one or more safety valves are arranged in the gas collecting zone, each safety valve defining an inlet which is fluidly connected to the interior of the gas collecting zone and an outlet which is fluidly connected to air outside the apparatus; and
   wherein at least one of the one or more safety valves is a liquid based safety valve and wherein the collecting member is arranged to cause the collected gas cooling liquid to flow into the liquid based safety valve whereby a predetermined liquid level in the liquid based safety valve is maintained.

2. The apparatus according to claim 1, wherein the collecting member is arranged with respect to an inner wall of the gas collecting zone such that gas and/or foam may pass between the inner wall and the highest point of the collecting member.

3. The apparatus according to claim 1, wherein the collecting member defines an upper and a lower surface and wherein a thermal insulator is provided between the upper and the lower surface.

4. The apparatus according to claim 1, wherein the collecting member is inclined relative to a horizontal direction so as to guide the collected gas cooling liquid towards the at least one liquid based safety valve.

5. The apparatus according to claim 1, wherein the collecting member is arranged such that the gas cooling liquid which is collected during use drips into the liquid based safety valve.

6. The apparatus according to claim 1, wherein the lowest point of the collecting member is positioned directly above the inlet of the liquid based safety valve(s).

7. The apparatus according to claim 1, wherein during operation of the apparatus, a vertical line extends through the lowest point of the collecting member and a liquid surface of the liquid based safety valve.

8. The apparatus according to claim 1, wherein the liquid based safety valve defines a liquid outlet, and wherein the liquid outlet is arranged to allow excess liquid from the liquid based safety valve to exit the liquid based safety valve therethrough.

9. The apparatus according to claim 1, wherein the liquid based safety valve defines a first and a second liquid trap which are arranged in series.

10. The apparatus according to claim 1, wherein the liquid based safety valve is accessible from an outer surface of the apparatus.

11. The apparatus according to claim 1, wherein the liquid based safety valve is slidably arranged in the apparatus such that that it is slidable between an inserted position in which it is positioned inside the apparatus in the gas collecting zone thereof, and a removed position in which it is accessible outside the apparatus.

12. The apparatus according to claim 9, wherein the liquid based safety valve defines a gas outlet which is arranged such that gas will escape the liquid based safety valve therethrough when the first liquid trap does not contain a predetermined amount of liquid.

13. The apparatus according to claim 9, wherein the first and the second liquid traps defines a first and a second liquid zone, respectively, in which liquid is provided during operation, and wherein the first and the second liquid zones are fluidly connected such that when a by-pass valve is in an open state liquid may flow from the first liquid zone to the second liquid zone, while liquid is prevented from flowing from the first to the second liquid zone through the by-pass valve, when the by-pass valve is in a closed state.

14. The apparatus according to claim 9, wherein the nozzles are adapted to function as fire and/or explosion preventing means.

15. The apparatus according to claim 9, wherein the nozzles are arranged such that when the gas cooling liquid is sprayed out through the nozzles, the gas cooling liquid is sprayed into a foam which during use of the apparatus is generated by the organic material whereby it ascends from the gas generating zone into the gas collecting zone in which it continues towards the one or more biogas outlets, the one or more nozzles being adapted to spray an amount of the gas cooling liquid sufficient to prevent the foam from entering the biogas outlet.

16. The apparatus according to claim 15, wherein the collecting member is arranged relative to the liquid based safety valve such that gas and/or foam is prevented from passing between the collecting member and the liquid based safety valve.

* * * * *